(12) United States Patent
Pagnoux et al.

(10) Patent No.: US 7,339,013 B2
(45) Date of Patent: Mar. 4, 2008

(54) THERMOSENSITIVE POLYMERS AND THERMOREVERSIBLE GELS OBTAINED FROM THESE POLYMERS

(75) Inventors: Anne Pagnoux, Le Barp (FR); Marc Dolatkhani, Cestas (FR); Patricia Chaffaux, Pessac (FR)

(73) Assignee: Polymerexpert SA, Pessac (FR)

( * ) Notice: Subject to any disclaimer, the term of this patent is extended or adjusted under 35 U.S.C. 154(b) by 0 days.

(21) Appl. No.: 11/010,929

(22) Filed: Dec. 13, 2004

(65) Prior Publication Data

US 2005/0175573 A1 Aug. 11, 2005

Related U.S. Application Data

(63) Continuation-in-part of application No. PCT/FR03/01786, filed on Jun. 13, 2003.

(30) Foreign Application Priority Data

Jun. 14, 2002 (FR) .................. 02 07463

(51) Int. Cl.
*C08G 18/00* (2006.01)
*C08G 18/48* (2006.01)
*C08F 287/00* (2006.01)
*C08F 291/06* (2006.01)

(52) U.S. Cl. .................. 525/528; 525/92 C; 525/111; 525/123; 525/124

(58) Field of Classification Search .................. None
See application file for complete search history.

(56) References Cited

U.S. PATENT DOCUMENTS 4,611,083 A * 9/1986 Buethe et al. .............. 560/351
5,120,816 A 6/1992 Gould et al.
5,183,876 A 2/1993 Kopp et al.
5,694,806 A 12/1997 Martin et al.

FOREIGN PATENT DOCUMENTS

| | | |
|---|---|---|
| EP | 0963796 | 12/1999 |
| GB | 2276627 | 10/1994 |
| WO | WO 95/26993 | 10/1995 |
| WO | WO 9526993 A1 * | 10/1995 |
| WO | WO 99/47072 | 9/1999 |
| WO | WO 9947072 A1 * | 9/1999 |

OTHER PUBLICATIONS

Odian, G. "Principles of Polymerization, 3rd edition" John Wiley & Sons, INC.: New York, 1991, pp. 56-59, 66-68, 136-138, and 148-149.*

* cited by examiner

*Primary Examiner*—Johann R. Richter
*Assistant Examiner*—James H Alstrum-Acevedo
(74) *Attorney, Agent, or Firm*—Lucas & Mercanit, LLP

(57) ABSTRACT

Polymers which comprise polymer chains of terpolymer type which are constituted by poly(ethylene oxide) (PEO) and poly(propylene oxide) (PPO) of PEO-PPO-PEO form, which are modified at their termini by groups which can essentially be other chains of PEO-PPO-PEO, acid segments, amine groups or PEOs, these chains being linked to the terpolymer chains via chemical bridges which are constituted by urethane bridges, urea bridges, allophanate bridges and biuret bridges, and which comprise more than 80% by weight of said PEO-PPO-PEO.

Thermoreversible physical gels of high viscosification index, which contain these polymers, and their uses.

Preparation of these polymers and of these gels.

33 Claims, 4 Drawing Sheets

THERMOSENSITIVE POLYMERS AND THERMOREVERSIBLE GELS OBTAINED FROM THESE POLYMERS

This Application is a Continuation-in-Part Application of the International PCT Application PCT/FR03/01786 filed on 13th Jun. 2003, which in turn claims priority of French Patent Application 02/07463 of 14th Jun. 2002.

FIELD OF THE INVENTION

The present invention relates to a thermosensitive polymer which can form thermoreversible gels of high viscosification index, as well as to their preparation. The invention also relates to applications of these gels.

Fields of application envisaged for these thermoreversible gels are, notably but not exclusively, therapeutic or non-therapeutic compositions, particularly cosmetic compositions, for the treatment of the human or animal body.

BACKGROUND OF THE INVENTION

Compositions of reversible gellification are defined as solutions the variation in viscosity of which is linked to a modification of the environmental conditions. When this modification of viscosity intervenes during a change in temperature, mention will be made of thermoreversible gels and the polymers constituting the formulation are identified as "thermogelling polymers" or even "thermosensitive polymers". These polymers are made up of hydrophobic, thermosensitive parts and hydrophilic parts. The formation of gel is explained by the auto-association of the thermosensitive portions in hydrophobic micro-domains; the entirety of the polymer being maintained in solution by the hydrophilic segments. The properties of viscosification and those of the gel are thus controlled by the respective length of the various segments and by the hydrophobic/hydrophilic ratio (L. E. Bromberg, Adv. Drug Delivery Reviews 31, (1998), 197-221).

Thermosensitive polymers are known which are intended to form thermoreversible gels in aqueous solution, the viscosity of said gels evolving reversibly as a function of their temperature. These thermosensitive polymers have hydrophobic portions which can aggregate together to form micelles when the temperature of the medium is high in order to attain that of their critical solution temperature; the hydrophilic portions linking said micelles between them. By virtue of this, an increase in the temperature of the aqueous medium in which these thermosensitive polymers are dissolved can convert it from a liquid state to a viscous state forming a gel.

Such polymers are well-known under the generic name of poloxamers. These are copolymers of blocks of propylene oxide and ethylene oxide, or polyoxyalkylenes, which can be synthesised notably according to the methods described in US patents U.S. Pat. No. 4,188,373 and U.S. Pat. No. 4,478,822. The thermosensitive polymers thus obtained enable formulating aqueous compositions which have critical solution temperatures of between 24 and 40° C. However, such formulations necessarily contain 15 to 50% of thermosensitive polymers in order to obtain a significant variation in the viscosity such that they are initially extremely viscous.

Furthermore, despite the high percentage of thermosensitive polymers that they contain, these formulations have only variations in viscosity which are less than a decade at their critical solution temperature.

More recently, pieces of work have been carried out in order to obtain compositions combining properties of thermogelling and bioadhesivity. In this light, several patents have claimed formulations of reversible gellification which are made by simple physical mixtures of a thermogelling polymer (a poloxamer) and a pH-sensitive polymer, selected from poly(carboxylic acids) (Carbopol) (U.S. Pat. No. 5,252,318, FR 2,802,097 and EP 0 551 626). At the critical solution temperature, (LCST—Lower Critical Solution Temperature), the variation in viscosity observed is about 5 to 8 times the initial viscosity, but the minimum concentration required remains high: at least 12% by mass of polymers. Poly(acrylic acids) have been mainly used for their property of adhesivity. In these latter innovations, segments of poly(acrylic acids) were chemically associated with segments of poloxamers. In addition to the bioadhesive and "pH sensitive" character, the poly(acrylic acid) part confers to the material a greater solubility in water. The presence of the hydrophilic segment promotes the solubilisation of the copolymer and thus limits the phase separation. It appears that the alternating copolymers of thermo- and pH-sensitive monomers rapidly loose their thermogelling property when the pH-sensitive monomer content increases; block copolymers are preferred.

The International Application WO 95 24430 describes graft copolymers or block copolymers of poly(acrylic acid)s (PAA) and thermosensitive polymers. The thermosensitive component of the material is ensured by Pluronics® polymers or poly(isopropylacrylamide) (NIPAm). According to the level of ionisation of the carboxylic functions, the stability of the gels and the value of the critical gellification temperature are slightly different.

The copolymerisation is carried out either by a reaction of condensation of the acid functions of the PAA with the modified reactive terminus of the Pluronic (monoamination of the hydroxy-termini)—the Pluronic-g-poly(acrylic acid) copolymer has thermosensitive grafts—, or by reaction of condensation between the poly(acrylic acid) and the poly(isopropylacrylamide), both of which are modified at a terminus by inter-condensable functions (amine and acid)— the Pluronic-b-poly(NIPAm) copolymer is formed by two blocks linked chemically.

In comparison to the physical mixtures of poloxamers and polyacids, the thermoreversible gellification of Hoffman copolymers (WO 95 24430) is obtained with compositions of lower concentrations of polymer: the formulations which contain 1 to 3% by mass of copolymer have a well-defined critical gellification temperature range of between 20° C. and 40° C., for a pH range of 4 to 8.

However, the variation in viscosity for these compositions does not attain a decade, and a phase separation into micro-domains is observed at the critical gellification temperature, and this manifests itself as an opacification of the medium. Moreover, the syntheses are carried out in several steps: a controlled modification of the terminal functions of the polymers used, condensation or chain copolymerisation, and finally separation/purification of the products desired.

After these pieces of work, Bromberg et al. described comb copolymers of poly(acrylic acid) and poloxamer, and their novel route to obtaining them (WO 97 00275). In a first step, radicals are created on the poloxamer chain by abstraction of hydrogen on the segment of poly(propylene oxide). The radical chain polymerisation of the acrylic acid is then initiated from poloxamer monoradicals.

The system obtained, which is called Smart Hydrogel™, has a perfect clarity before and at the gellification point; the sol-gel transition of aqueous solutions of low concentrations of copolymers (1 to 5% by mass) is produced in a narrow temperature interval (10° C.), between 25 and 40° C. and manifests itself by an increase in viscosity of about at least 30 times the initial viscosity. The gel thus formed behaves as a viscoelastic solid and keeps its viscosity whatever the shearing speed applied.

Two drawbacks in relation to this system were revealed by the inventors of the present invention: the bioadhesivity of the hydrogel is limited by a poor accessibility of the poly (acrylic acid) parts and the compositions have a reduced stability due to the initial oxidation of the Pluronic® polymer to create the initiating radical.

In order to improve these properties, Bromberg et al. have provided novel linear block copolymers in keeping the poloxamer and the poly(acrylic acid), as thermosensitive compound and hydrophilic compound, respectively. The originality of these copolymers is that they are composed of a central poloxamer block which is modified at its two termini by polyacid blocks. To obtain them, the two termini of the poloxamer are functionalised beforehand by acrylic or thiol groups which enable the initiation of the radical polymerisation of the acrylic acid. These triblocks show a reversible gellification at body temperature (25-40° C.), at values of pH of between 3 and 13. The solutions which are of low concentration (1 to 4% by mass) thus undergo an increase in viscosity which can go up to 2 decades.

Here again, however, the synthetic route selected is a multi-step one and it is necessary to remove the residual monomers, during or at the end of manufacture, by major treatments (extraction by Soxhlet, dialysis, multiple precipitations . . . ).

Thus, several reversible gellification systems are known to this day. Nevertheless, they necessitate a high content of solid and/or lead to a low gain in viscosity of the formulations at the LCST. Finally, the most recent systems are obtained from poloxamers having modified termini, and this necessitates multi-step syntheses and separation/purification operations which are not very compatible with an industrial production method.

SUMMARY OF THE INVENTION

The present invention provides thermosensitive polymers which enable obtaining not only thermoreversible physical gels with a low concentration of polymer, but also thermoreversible physical gels of high viscosification index, the viscosity of which increases strongly at their critical solution temperature.

The term "physical gel" is understood as meaning a gel which results from the association of polymer chains by virtue of the formation of non-covalent bonds of ionic, dipolar, hydrogen bond or hydrophobic interaction type, between the chains.

Further, an aim of the present invention is also to provide thermosensitive polymers which enable obtaining gels which are thermoreversible at temperatures which are approximately equal to the body temperatures, in order to form effective cosmetic and pharmaceutical compositions.

More specifically, the invention relates to polymers which comprise polymer chains of terpolymer type which are constituted by poly(ethylene oxide) (PEO) and poly(propylene oxide) (PPO) of PEO-PPO-PEO form, which are modified at their termini by groups which can essentially be other chains of PEO-PPO-PEO, acid segments, amine groups or PEOs, these chains being linked to the terpolymer chains via chemical bridges which are constituted by urethane bridges, urea bridges, allophanate bridges and biuret bridges, and which comprise more than 80% by weight of said PEO-PPO-PEO. All these bridges can be present either in a same polymer chain, or in different chains, and, as emerges from the following disclosure, the proportion of these various bonds essentially depends upon the operating conditions. As emerges from the following disclosure, as a function of the proportions of the various reagents, access is in fact made either to linear type polymers in which the polyoxyalkylene chains of terpolymer type are extended essentially via chemical groups which are linked to them by carbamate and urea type bridges, or to branched polymers additionally having groups of allophanate and/or biuret type.

Now, it has appeared to the inventors of the present invention that the presence in these polymers of urea type bonds and optionally of biuret type greatly improved the properties of the gel formed from these polymers, due to the creation of additional hydrogen bonds between the various polymer chains.

DETAILED DESCRIPTION OF THE INVENTION

Figure 1:
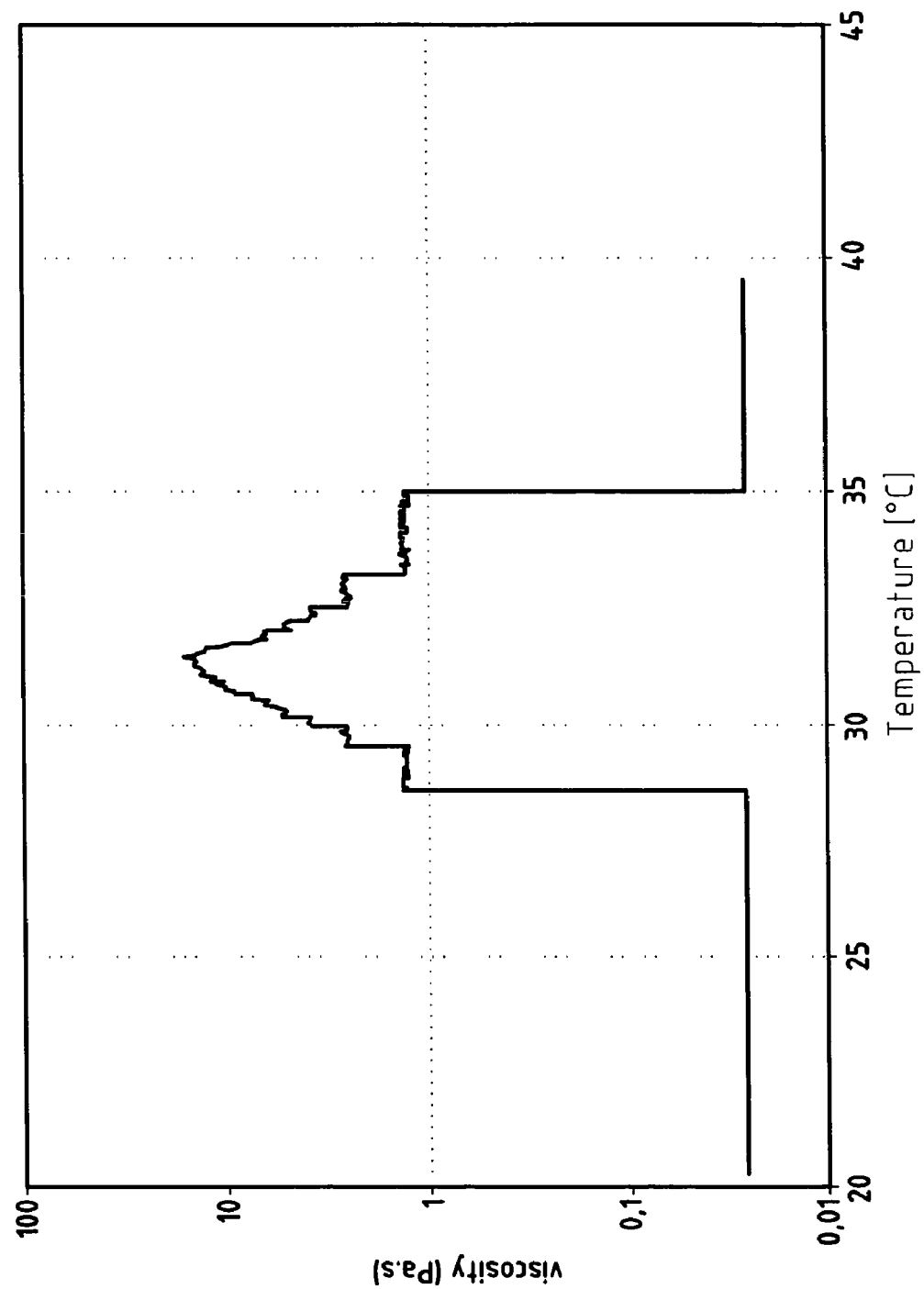
FIG. 1 illustrates the viscosity curve of a gel obtained according to Example 1.

According to a first object, the present invention provides a hydrosoluble thermosensitive polymer which has a low viscosity at ambient temperature in solution, which can form thermoreversibl.e physical gels of high viscosification index at temperatures of greater than 25° C., and which comprises more than 80% by weight of thermosensitive polyoxyalkylene triblock type linear chains consisting of blocks of poly(ethylene oxide) (PEO) and of blocks of poly(propylene oxide) (PPO), said chains being of PEO-PPO-PEO form, linked together via carbamate bonds and urea bonds.

According to a preferred embodiment of said object, the thermosensitive polymer comprises at least one PEO-PPO-PEO chain which is extended at at least one of its termini by an organic group via a carbamate bond, and chains which are constituted of at least one PEO-PPO-PEO chain which is extended at at least one of its termini by an organic group via a urea bond.

Thus, a characteristic of the thermosensitive polymer according to the invention resides in the extension of the linear chain of the thermosensitive polyoxyalkylenes and in the introduction of urea groups in the polymer chain, so as to confer to them a higher molecular weight and to provide them with novel functions which can induce additional interactions of hydrogen bond type. The extension is thus carried out by linking the organic groups to the linear chains via carbamate and urea bonds. By virtue of this, by virtue of the thermosensitive polymers of higher molecular weight containing urea bridges, the viscosity of the gels that they enable formulating, at their critical solution temperature, is increased.

Advantageously, the structure of said thermosensitive polymer comprises at least one linear chain of thermosensitive polyoxyalkylene type which is constituted of three blocks (poly(ethylene oxide)-poly(propylene oxide)-poly(ethylene oxide)) and which is extended at both of its two termini by an organic group via a carbamate or urea bond. By virtue of this, the molecular weight of the polymer is increased more, and novel groups which can form interactions of hydrogen bond type are introduced into the polymer chain, and this confers an even greater viscosity to the gels formulated, at the critical temperature, without the viscosity of the gel being significant away from this critical solution temperature.

According to a particularly advantageous embodiment of the invention, said linear chains of thermosensitive triblock polyoxyalkylene type are of formula:

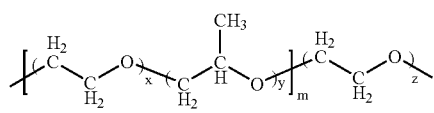

in which, $20<x<120$, $20<y<120$, $20<z<120$, and $m>0$. Thus, the polyoxyalkylene chain has a linear propylene oxide block each terminus of which is linked to a block of ethylene oxide. Preferably, the linear polyoxyalkylene chain is symmetrical, m being equal to 1 and x being approximately equal to z. These are the termini of the chain which are linked to the organic group via carbamate and/or urea bonds.

Particularly advantageously, said organic groups contain radicals which can be linked to the polyoxyalkylene chains via a carbamate or urea bond, and are selected from:

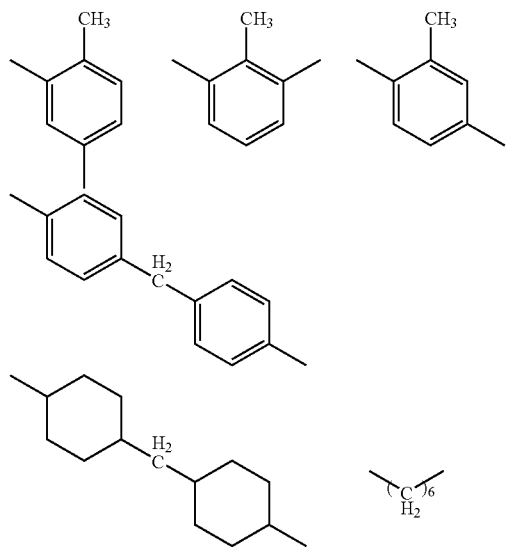

Thus, according to this feature of the invention, the organic groups contain at least one of said radicals, notably at one of its termini.

The radical is linked firstly to the polyoxyalkylene chain via a carbamate or urea bond, and secondly to another molecule, also via a carbamate or urea group.

According to a variant of the invention, the organic groups contain at least one of said radicals and acid moieties which are linked together via carbamate or urea bonds. By virtue of this, the acid moiety is spaced from the polyoxyalkylene chain via one of said radicals, which is linked to the polyoxyalkylene chain and to the acid moiety via two distinct carbamate or urea bonds. It is understood additionally that the organic group can be constituted alternatively by said radicals and by the acid moieties, and that it can by extended at both of the termini of said polyoxyalkylene chain, or that it can group together between them two of said polyoxyalkylene chains. By virtue of this, by virtue of the acid functions of said moiety, the thermosensitive polymer, which is an object of the invention, gets its rheological properties varied, not only as a function of the temperature but also as a function of the pH of the medium in which it is. Moreover, the presence of the acid group confers the property of bioadhesivity to the thermosensitive polymer.

According to another advantageous variant, said organic group contains said radicals and tertiary amine moieties which are linked together via carbamate or urea bonds. Thus, the amine functions which can capture a proton enable the properties of the polymer to be varied as a function of the acidity of the medium.

Additionally, preferably, the organic group alternatively contains at least one sequence: radical, amine moiety, radical and acid moiety, the elements of this sequence being linked two-to-two via a carbamate or urea bond.

According to another particular embodiment of the invention, said organic group contains a chain of poly(ethylene oxide) type. This poly(ethylene oxide) chain can be spaced from the thermosensitive polyoxyalkylene chain by one of said radicals and linked to the latter via a carbamate or urea bond. Additionally, the poly(ethylene oxide) chain which advantageously has a molecular weight of less than 1,000 can be associated with acid or amine moieties in the organic group.

Particularly advantageously, said organic group has branches which are constituted via allophanate or biuret bonds. These bonds which are formed, as will be explained more in detail in the description of the synthetic method, by the reaction of an isocyanate function with a carbamate or urea bond, which lead to branches by virtue of the tri-substituted nitrogen of the carbamate or urea bond. Thus, the radicals can be linked between themselves by virtue of the allophanate or biuret bonds. Additionally, particularly advantageously, the improved thermosensitive polymer comprises a plurality of linear chains of thermosensitive polyoxyalkylene, triblock type which are linked together via one or more organic groups via carbamate or urea bonds, either linearly, the linear polyoxyalkylene chains being spaced from each other via organic groups, or branched by virtue of the allophanate or biuret bonds.

Moreover, it is understood that the organic groups can contain acid, amine moieties, or polyoxyethylene chains.

According to a second object, the present invention provides a method of synthesising an improved thermosensitive polymer which can form thermoreversible physical gels of high viscosification index and, more particularly, polymers which are defined above, which method comprises the reaction of at least one linear polymer P of thermosensitive polyoxyalkylene triblock type having at least one terminal hydroxy function with at least one organic molecule which bears at least one isocyanate function, so as to link them together via carbamate or urea bonds.

This synthesis is carried out particularly simply in a solvent medium in one sole step and without intermediate purification of the polymers P which in general contain at least some traces of water the presence of which enables bonds of urea type to be introduced into the chains formed during the reaction.

As emerges from the following, with the view to increasing the proportion of urea bonds, it is possible to add water into the reaction medium at a rate of a total amount of water preferably of 0.1% to 0.6% by mass with respect to the terpolymer, more preferably of 0.3 to 0.6%.

Thus, a feature of the invention is to extend a linear polymer P of thermosensitive polyoxyalkylene triblock type having at least one terminal hydroxy function in reacting isocyanate functions with the hydroxy functions of the polymer P in the presence of water.

Advantageously, said polymer P has at least two terminal hydroxy functions so as to be able to be extended at each one of its termini.

According to a particularly advantageous embodiment of the invention, said polymer P is of generic formula:

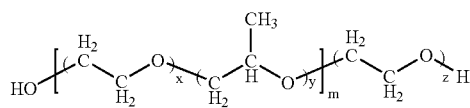

in which, 20<x<120, 20<y<120, 20<z<120, and m>0. Preferably, m is equal to 1 and x equal to z.

Advantageously, the organic molecule comprises two isocyanate functions, such that one sole organic molecule can link two molecules between them which comprise hydroxy groups via two carbamate or urea bonds which are obtained by a reaction of condensation of the isocyanate functions and hydroxy functions, in the presence of water.

According to a preferred embodiment of the invention, the organic molecule is selected from:

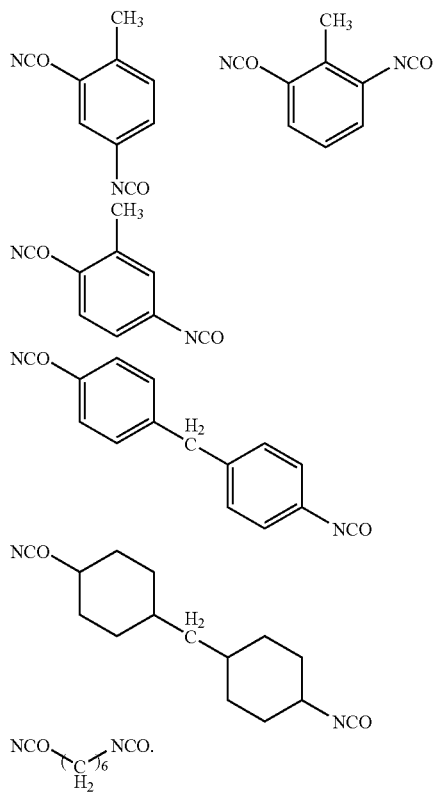

The choice of such or such an organic molecule enables a rate of condensation reaction to be obtained which is more or less fast, by virtue of the choice of an organic molecule having at least one benzene ring or non-benzene ring, and by virtue of the position of the isocyanate function on the ring. By virtue of this, various thermosensitive polymers can be obtained.

According to another preferred embodiment of the invention, said reaction is carried out in the presence of at least one other organic molecule which bears at least one hydroxy function, advantageously two, in the presence of water. Thus, by virtue of the two isocyanate functions of the organic molecules, said other organic molecule can be linked to the organic molecule via a carbamate or urea bond, which itself is linked to said chain of said linear polymer P of thermosensitive polyoxyalkylene type. Moreover, when said other molecule has two hydroxy functions, it is understood that said thermosensitive polymer can be extended at each one of its termini, alternatively, by an organic molecule having two isocyanate functions and another molecule, the organic molecules being linked to the other organic molecules via carbamate or urea bonds.

In a particular embodiment of the invention, according to said other preferred mode, and preferably, said other organic molecule further comprises at least one carboxylic acid function, advantageously two. By virtue of this, it is easy to produce improved thermosensitive polymers which are sensitive to the variations in pH and the viscosity of the gel of which that it enables realising evolves not only with temperature but also with the acidity of the medium.

Advantageously, said other molecule is of formula:

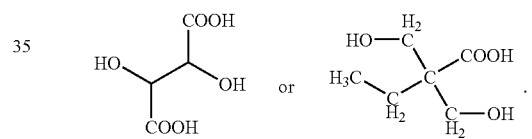

In parallel to said particular embodiment of the invention that precedes, said other organic molecule advantageously comprises at least one tertiary amine function which also provides the gels formulated with the improved thermosensitive polymer with a sensitivity to the variations in pH. Advantageously, said other molecule is of formula:

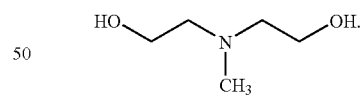

According to said other preferred embodiment of the invention and advantageously, said other molecule is a monohydroxylated poly(ethylene oxide) which can increase the stability and the properties of viscosification of the gel containing said improved thermosensitive polymer.

According to a third object, the present invention provides an improved thermosensitive polymer which has, in solution, a low viscosity at ambient temperature and which can form thermoreversible physical gels of high viscosification index for temperatures higher than 25° C. Its structure comprises at least one thermosensitive polyoxyalkylene triblock type linear chain which is extended at one of its termini at least by an organic group via a carbamate or urea bond. It can be obtained by a synthetic method which comprises the reaction of at least one linear polymer P of thermosensitive polyoxyalkylene triblock type having at least one terminal hydroxy function with at least one organic molecule which bears at least one isocyanate function, in the presence of water, so as to link them together via said carbamate or urea bond.

According to a fourth object, the present invention provides a thermoreversible gel which comprises at least one thermosensitive polymer in accordance with the first object, or at least one thermosensitive polymer obtained according to a synthetic method in accordance with the second object.

The gel formed is a physical gel.

The thermoreversible gel of the invention contains 1 to 10% by weight of said improved thermosensitive polymer and more advantageously 1 to 5% of said improved thermosensitive polymer which is obtained in the presence of water and which thus contains urea groups.

According to a fifth object, the present invention provides a pharmaceutical or non-pharmaceutical composition, particularly a cosmetic composition, which is intended for treating or for a care of the human body, comprising a product in solution of low viscosity with temperature and which can form a thermoreversible physical gel of high viscosity at temperatures of greater than 25° C. according to said fourth object.

According to a sixth object, the invention relates to a prosthetic element which can be inserted into an organ of the human body, characterised in that it comprises a thermoreversible gel according to said fourth object.

Other particularities and advantages of the invention will emerge upon reading the detailed description made below of particular embodiments of the invention, which are given as an indication, but non-limiting, as well as the Examples and the Figures.

The invention relates to improved thermosensitive hydrosoluble copolymers, which are linear or branched and which have in solution a low viscosity at ambient temperature and which can form thermoreversible gels of high viscosification index at temperatures of greater than 26° C., and to a method of synthesis of such polymers. Further, the invention also relates to the application of such a thermoreversible gel.

According to the invention, improved thermosensitive hydrosoluble polymers are synthesised which enable thermoreversible gels to be obtained the viscosity of which increases by at least a factor of a 1,000 when the temperature exceeds 25° C. for concentrations of thermosensitive polymers in water of less than 10%. The synthesis of the improved thermosensitive polymers is carried out from well-known thermosensitive copolymers: polyoxyalkylenes or poloxamers having terminal hydroxy functions. The copolymers selected are triblocks and are of the generic formula:

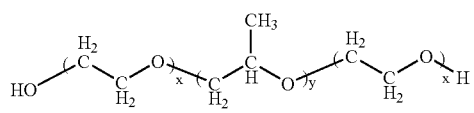

in which, $20<x<120$ and $20<y<120$. These thermosensitive polymers, which are marketed for example under the name of Pluronics, contain 25% by mole of propylene oxide moiety and enable an increase in the viscosity to be obtained of only a factor of 10 when the temperature increases from 20° C. to 30° C. for concentrations of greater than 15% in water.

Obviously, a mixture of these types of thermosensitive polymers can be used for preparing improved thermosensitive polymers.

The inventive concept of the invention resides notably in the coupling of the well-known thermosensitive polymers with organic groups the size of which is smaller than that of said polymers. These couplings can be obtained by reaction of organic compounds of diisocyanate type with the hydroxy functions of the thermosensitive polymer in the presence of water, in order to form urethane and/or urea bonds, as well as allophanate and/or biuret groups. Moreover, the methods to be implemented are simplified, since the syntheses can be carried out in the same reactor, the diisocyanates reacting by polycondensation with the hydroxy functions of the thermosensitive polymers, without a step of removal of the traces of water which are usually present in the copolymers of polyoxyalkylene type.

Thus, in a reactor equipped with mechanical agitation, a condenser and a nitrogen inlet, the triblock polymer PEO-PPO-PEO is dissolved in a solvent, preferably butanone, at a temperature of the order of 70° C. The diisocyanate is introduced dropwise. At the end of the addition, the catalyst is added. The reaction is carried out at 70° C. under agitation until complete disappearance of the isocyanates.

The advantage of the synthesis is that it is carried out in one step in a single reactor. The second advantage of this synthesis is that it is carried out from commercial constituents, without any supplementary purification step. Thus, the triblock copolymer PEO-PPO-PEO is used without being dried. In general, it contains then 0.3%+/−0.05% by mass of water and this water leads, during the synthesis, to the formation of urea bridges. It is in this specific case that the thermogelling polymers obtained are the most effective since there is, in addition to the urethane and allophanate bridges, urea and biuret bridges which can give rise to hydrogen bond type interactions which add to the hydrophobic interactions of the PPOs. A drying of the copolymer can nevertheless prove to be necessary for a perfect control of the water content (variable according to the providers) which is introduced into the reaction medium. In this case, a specific amount of water is added at the start of the reaction.

It is noted that the amount of water which is acceptable for forming thermogelling polymers is advantageously 0.1 to 0.6% by mass with respect to the terpolymer. At 0.6% of water, the viscosity of the solution of our polymer is slightly greater than that of the other solutions of improved polymer, but the viscosity of the corresponding gel is also greater than that of the other gels. There is therefore a beneficial effect of the water (and by that even of the urea groups) upon the capability of the polymers to gellify aqueous solutions at temperatures of greater than 25° C.

The most effective polymers (the most capable of making the water gellify) are those which are obtained with 0.3 to 0.6% of water, which is introduced at the start of the synthesis into the reaction medium via the constituents and/or by adding water.

These polymers can then be used alone, preferably at the rate of 3.5 to 5% by mass into the aqueous solutions.

In association with the compounds such as cross-linked polyacids of CARBOPOL type, the improved polymer can be used at less than 3% and preferably at between 1% and 2.5%. This effect of synergy is obtained with 0.05% to 1% of cross-linked polyacid.

In the case of polymers which are prepared under anhydrous conditions (drying of the PEO-PPO-PEO), the amount of polymer to be used would be of at least 10% by mass in order to attain the same gain in viscosity.

The most effective polymers are obtained with 0.3% of water by mass with respect to the mass of triblock polymers and with acid functions or POE on the chain, with an NCO/OH ratio=1.1/1 (in taking into account the provision of water contained in the triblocks or 2/1 without counting the water).

The properties of increase in viscosity with temperature can be adjusted as a function of the concentration of water in the reaction medium and therefore as a function of the proportion of urea, biuret, allophanate and urethane groups.

The diisocyanates which can be used for the synthesis of the improved thermosensitive polymers are notably the following compounds:

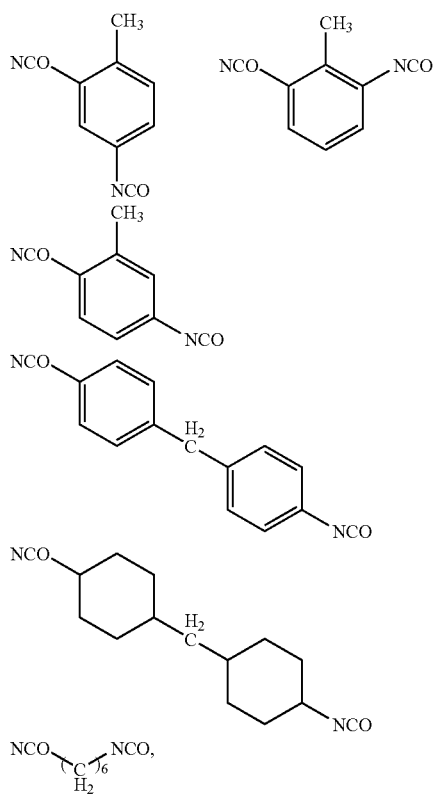

which are selected as a function of the reaction kinetics, and consequently of the final polymer that is desired to be obtained.

Further, as will be explained in greater detail in the description that follows, they enable inserting other functionalities, into the organic groups linking the polyoxyalkylene chains, which notably enable the gel formulated with the improved thermosensitive polymer to be rendered sensitive to the pH of the medium.

However, as will be explained in the description that follows, one of the important advantages of the diisocyanates is being able to introduce branches into the organic groups linking the thermosensitive polymers, and also urea groups which can form additional interactions by hydrogen bonds between the thermosensitive polymer chains.

As set forth above, the polymers of the invention are either linear or branched.

The structure of linear improved thermosensitive polymers will be described first of all in general terms and then particular examples of methods of synthesis will be given. Then, branched improved thermosensitive polymers will be described with particular examples, in the Example part.

A first type of improved thermosensitive polymer has the general formula:

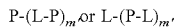

in which $1 \leq m \leq 5$.

The symbol P represents the thermosensitive polymer and is of form:

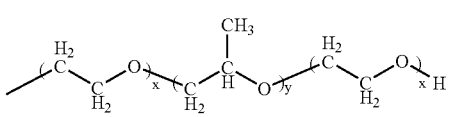

if it is situated at the terminus of a chain, or of the form:

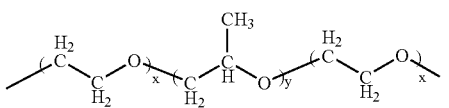

if it is situated in the polymer chain.

The symbol L, which corresponds to the organic group, is, in this first type of polymer, selected from:

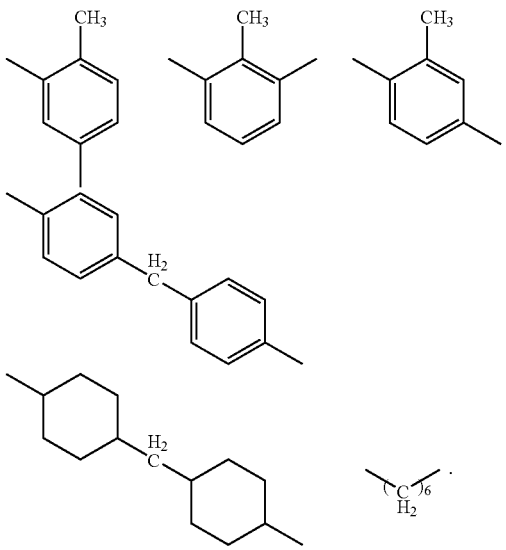

The group L and the thermosensitive polymers P are linked to each other via carbamate functions, and more particularly urethane functions of general formula:

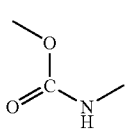

and/or via urea functions of general formula —NH—CO—NH. At the terminus of the chain, the group L can be terminated with a nitrogen-containing group.

A first example of synthesis of improved thermosensitive polymer corresponding to the first type of polymer described above is given in Example 1. The proportions of the various constituents and the implementation conditions are given for laboratory syntheses, but they can be adapted to industrial conditions by increasing the proportions and by adapting the implementation. This will be the case for all the synthesis examples described below.

A second example of synthesis of improved thermosensitive polymer corresponding to this first type of polymer is described in Example 2.

A second type of improved thermosensitive polymer according to the invention has the general formula:

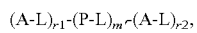

or

in which m', r1, r2≧1. P and L correspond to the structures described above. Preferably, r1 and r2 are, independently of each other, between 1 and 1,000.

The symbol A corresponds itself either to acid blocks or to tertiary amine blocks, or even to poly(ethylene oxide)s. This second type of polymer can also contain two of these different blocks or the three.

It is understood that the organic group linking the thermosensitive polymers can be constituted by a molecule link of L and A type which are linked to each other via carbamate functions. An advantage of the amino and carboxylic acid organic groups A is that they are ionisable and that the viscosity of the gel formulated with this second type of polymer varies with the pH of the medium. The advantage of the A groups which are composed of monohydroxylated poly(ethylene oxide) is that they enable a high stability of the gel formed, even at high temperature (25° C. to 50° C.).

Examples 3 and 4 below correspond to examples of synthesis of improved thermosensitive polymers which correspond to this second type of polymer.

A third type of improved thermosensitive polymer having branches can be obtained in accordance with the invention. These branches are formed by reaction of isocyanate functions with carbamate and/or urea functions in order to form allophanate bonds having the following structure:

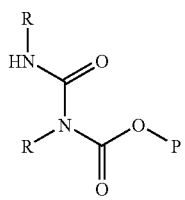

and/or biuret wherein the nitrogen N of the isocyanate function having initially reacted with the hydroxy function of the polyoxyalkylene is linked to the sp² hybridised carbon of a second isocyanate function.

According to this third type of polymer, examples of which are given in Examples 5, 6, 7, 8, and 9, a general form can be given by the following formula:

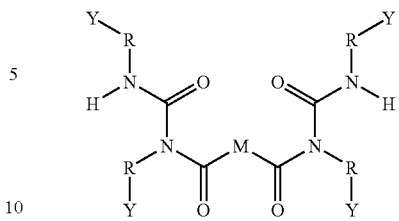

in which M can correspond to the first or to the second type of improved thermosensitive polymers as described in the examples corresponding to the two types of polymer above. R corresponds to the radical of the diisocyanate described above and Y can correspond to a terminal ethyl or methyl function, to an amino group or even to another improved thermosensitive polymer.

Thus, it is understood that not only can these polymers be branched by virtue of the allophanate or biuret bonds, but also that they can comprise a plurality of polyoxyalkylene which are linked together via organic groups which can comprise diisocyanates alone or diisocyanates coupled with acid, basic, or other blocks.

The improved thermosensitive polymers which are the object of the present invention have the double advantage of forming thermoreversible gels which have a great increase in their viscosity for relatively low concentrations, advantageously of the order of 5%. Additionally, by virtue of the various possibilities of synthesis, the temperature ranges in which the viscosity increases can be adjusted and they can be modulated as a function of pH.

The gels are obtained from a solution containing 1 to 10% of the polymer according to the invention, preferably 1 to 5%, preferably 3.5 to 5%.

The aqueous solution of the polymer can be obtained in two ways: from the precipitated polymer or by virtue of a change of solvent at the end of the synthesis of said polymer.

In the first case, the precipitated and dried polymer is added into water at a pH preferably of the order of 7, and the dissolution is carried out at a temperature close to ambient temperature (15-23° C.) for 12 to 24 hours. Anti-foaming agents can be added in order to limit the formation of foam and to thus accelerate the dissolution.

In the second case, at the end of the synthesis, when all the isocyanate functions have been consumed, water is added into the reaction medium and the organic solvent of the reaction is removed under vacuum. The amount of water at pH 7 initially introduced is calculated so as to obtain a dry extract of 3.5 to 5% after evaporation of the solvent of the reaction. This operation of transfer of solvent enables getting rid of the slow dissolution of the polymer.

The aqueous solutions of improved thermogelling polymers thus prepared are liquid at ambient temperature (dynamic viscosity between 35 and 100 cP) and gellify when their temperature is situated between 25° C. and 40° C. The gellification of the solution manifests itself by an increase in the viscosity of at least 3 decades (measurement made under a shearing of 0.3 s$^{-1}$) and the formation of a mass which can no longer flow. It is noted that the gel formed can be rapidly destructured if it is subjected to a significant shearing: it is rheofluidifying. This property is an advantage, notably for the cosmetic applications in which the thermogelling aqueous solution is diffused in the form of a spray. In fact, during this operation, the solution of improved thermosensitive polymer is strongly sheared and therefore very liquid, then, in contact with the skin the solution gellifies.

For pharmaceutical or cosmetic applications, the various active principles and specific agents can be formulated with 3.5 to 5% of the thermosensitive polymer, in aqueous solution, at ambient temperature. The liquid formulations below 25° C. can then be applied in the form of a spray on the skin, on the vaginal or nasal mucous membranes; the formulations will gellify upon contact. It will be possible for the creamy formulations to be spread on the skin and they will thicken upon stopping the friction. In these two examples, the gellification of the formulation will enable a controlled and progressive release of the active principles.

The increase in viscosity will also be able to be taken advantage of in order to stabilise the viscosity of solar creams or paints. In fact, if heat fluidifies the products cited, the presence of the thermosensitive polymer of the invention in the products enables the decrease in the viscosity to be compensated by its gellification (or here, its viscosification).

These polymers are formulated in aqueous solution in order to form pharmaceutical or non-pharmaceutical compositions, in particular cosmetic compositions which can notably be applied at low viscosity on the body and can then gellify by virtue of the increase in temperature.

A first example of application relates to the pharmaceutical preparations which comprise an improved thermosensitive polymer in accordance with the invention in solution in water and an active principle. This type of preparation is applied in more or less liquid form on the body and it then gellifies such that the active principle is distributed over all the surface of application and is maintained thereon by the gel. Ointments, for example, can be thus formulated. According to an embodiment, these preparations containing an active principle can be applied on the mucous membranes, notably on the vaginal or nasal mucous membranes, those of the stomach or of the oesophagus.

A second example relates to the preparations which are intended to be applied via the subcutaneous route in order to release an active principle slowly or in order to fill in spaces or cavities, e.g. wrinkles. Mammary prostheses can also be constituted by a gel which is formulated with a thermosensitive polymer according to the invention. Thus, the prosthesis can be introduced in liquid form, and this decreases the width of the incision necessary.

Another example of application relates to meatal blockages intended to block the lachrymal canal. The blockage is made by introducing, into the depth of the cavity, a solution containing a polymer according to the invention in liquid form at ambient temperature neighbouring 20° C. and in leaving it warm up to body temperature neighbouring 37° C. in order that it form a blockage in the depth of the cavity.

Yet another example of application relates to a coating or under-coating comprising at least a part containing a thermoreversible gel obtained from an aqueous solution containing an improved thermosensitive polymer according to the invention.

EXAMPLES

Example 1

In this Example, $3.8 \cdot 10^{-3}$ mole of a polymer bearing the reference F127 marketed under the name of Pluronic is dissolved in 150 ml of 2-butanone, the whole being brought to 70° C. The polymer F127 is introduced without purification and contains 0.3% by mass of water ($7.6 \cdot 10^{-3}$ mole).

$11.4 \cdot 10^{-3}$ mole of 4,4'-methylene biscyclohexyl di-isocyanate corresponding to the general formula:

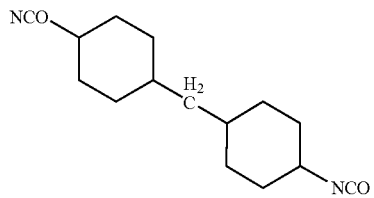

are then added dropwise to the mixture over 10 minutes under a continuous flow of nitrogen. A tin-based catalyst is introduced (at the rate of 500 ppm) into the mixture, which is maintained under reflux of the solvent over about 20 hours.

After the mixture has attained ambient temperature, of the order of 20° C., a determined amount of water is added to the reaction mixture so that the content of thermosensitive polymer thus synthesised correspond to 5% of the total weight. The 2-butanone contained in the mixture is removed in vacuo. The solution containing 5% by mass of improved thermogelling polymer thus obtained is ready for use.

FIG. 1 illustrates the viscosity curve of the thermoreversible gel obtained according to this first Example, as a function of the temperature under a shearing speed of 0.4/s. Thus, an advantage of this first Example of implementation of the invention resides in the increase in the viscosity of the gel by a value which is greater than 10 Pa·s in a temperature range of between 29 and 34° C. with a maximum value of the viscosity for around 32° C.

Example 2

This second Example of synthesis of improved thermosensitive polymer corresponds to the first type of polymer described above.

Only the stoichiometry of the reaction is more or less modified, the implementation being identical to the first Example. In this Example, $8.0 \cdot 10^{-3}$ mole of 4,4'-methylene biscyclohexyl di-isocyanate are introduced into the mixture.

The solution of this improved polymer is characterised by its transparency and by an increase by 5 decades of the viscosity, under a shearing speed of 0.01 s$^{-1}$, when its temperature attains 35° C.

Example 3

This example of synthesis of improved thermosensitive polymer corresponds to the second type of polymer described above.

The improved thermosensitive polymer comprises polyacid blocks and tertiary amino blocks.

The synthesis is carried out in two steps. In a first step, $3.8 \cdot 10^{-3}$ mole of non-dried F127 Pluronic polymer containing 0.3% by mass of water are dissolved with $7.7 \cdot 10^{-3}$ mole of N-methyldiethanolamine in 150 ml of 2-butanone. $2.3 \cdot 10^{-2}$ mole of 4,4'-methylene biscyclohexyl di-isocyanate are then added dropwise over 10 minutes under a continuous flow of nitrogen. $1.2 \cdot 10^{-2}$ mole of tartaric acid in solution in 2-butanone are then added after six hours' reaction at 70° C. The polycondensation is continued for 2 hours until the complete disappearance of the isocyanate functions. The polymer is collected either directly in the aqueous phase, or after transfer of solvent or even by precipitation in ether or hexane.

Figure 2:
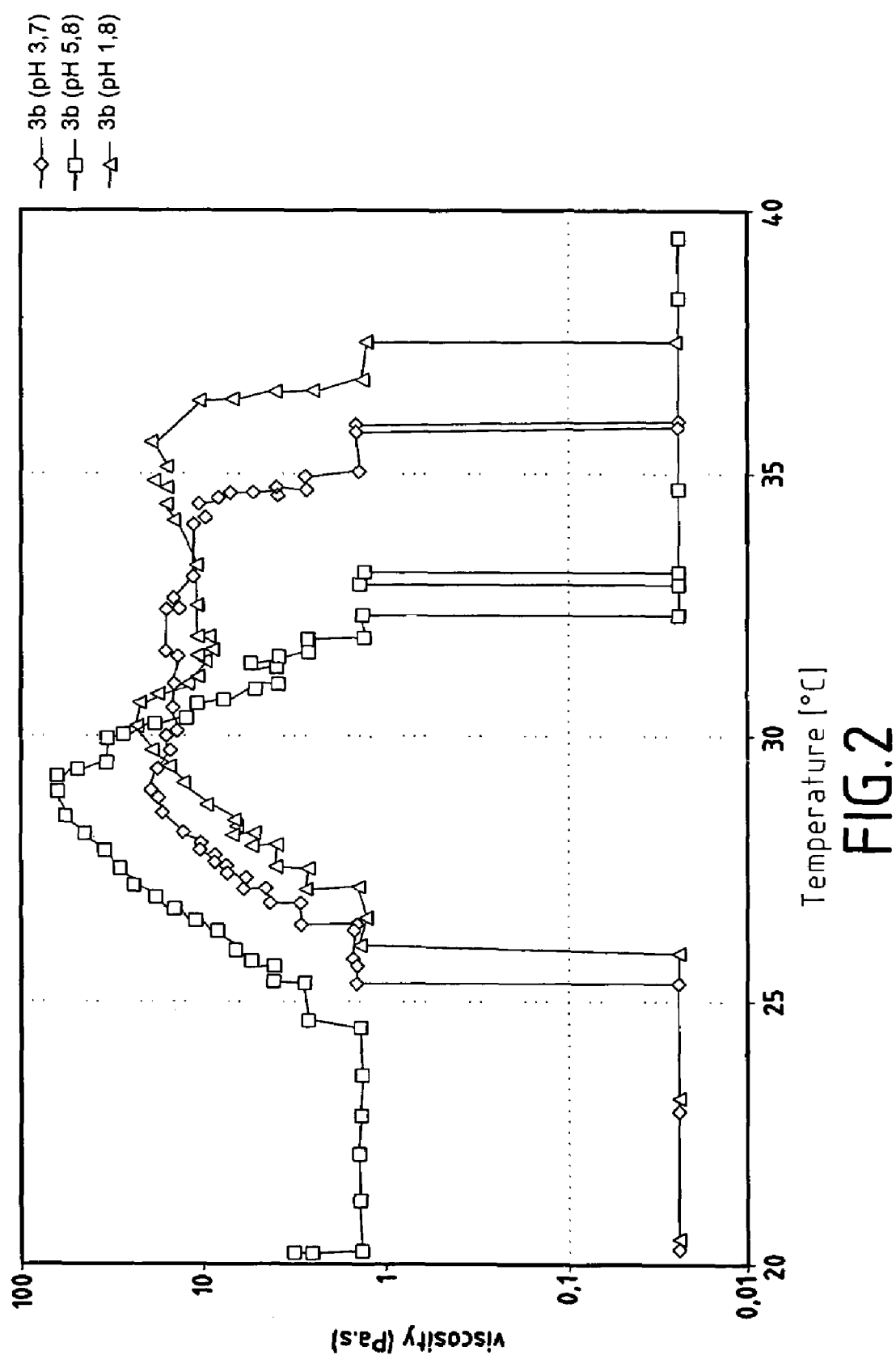
FIG. 2 illustrates the viscosity curves of a gel obtained according to Example 3.

FIG. 2 illustrates the variations in viscosity of the gel obtained with 5% by weight of the improved thermosensitive polymer synthesised in accordance with this Example. FIG. 2 has 3 curves which correspond to three different values of pH of the solution forming the gel: 3.7; 5.8; and 1.8.

At the value of pH of 5.8, the viscosity of the gel as a function of the temperature behaves similarly to the gel obtained with the improved thermosensitive polymer of the first Example, except that the maximum viscosity is greater and that it attains approximately 100 Pa·s at 29° C. under a shearing speed of $0.4\ s^{-1}$.

On the other hand, at a pH of 3.7, the maximum viscosity of the gel is lower, since it is less than 30 Pa·s, the curve forming a plateau between approximately 28 and 34° C.

At a pH of 1.8, the viscosity curve has more or less the same spread out form towards higher temperatures since the plateau extends between 30 and 36° C.

Thus, by virtue of the ionisable blocks of the improved thermosensitive polymer, it is possible to adjust the viscosity of the gel as a function of the acidity of the solution in which it is dissolved.

Example 4

In this example of synthesis of improved thermosensitive polymer corresponding to the second type of polymer described above, an improved thermosensitive polymer is described which comprises ionisable polyacid blocks which confer a marked bioadhesive character to the gel.

The synthesis is carried out in two steps. In a first step, $3.8 \cdot 10^{-3}$ mole of non-dried F127 Pluronic polymer containing 0.3% by mass of water are dissolved in 150 ml of 2-butanone. $1.5 \cdot 10^{-2}$ mole of 4,4'-methylene biscyclohexyl di-isocyanate are then added dropwise over 10 minutes under a continuous flow of nitrogen. When about 81% of the isocyanate functions are consumed, $2.9 \cdot 10^{-3}$ mole of 2,2-(bis hydroxymethyl)butyric acid are added. The polycondensation is continued for 24 hours at 70° C. until the complete disappearance of the isocyanate functions. The polymer is collected by precipitation in diethyl ether; the dynamic viscosity of a 5% solution of this polymer passes from 80 mPa·s at ambient temperature to 2,400 Pa·s at 35° C., under a shearing speed of $0.003 s^{-1}$.

Figure 3:
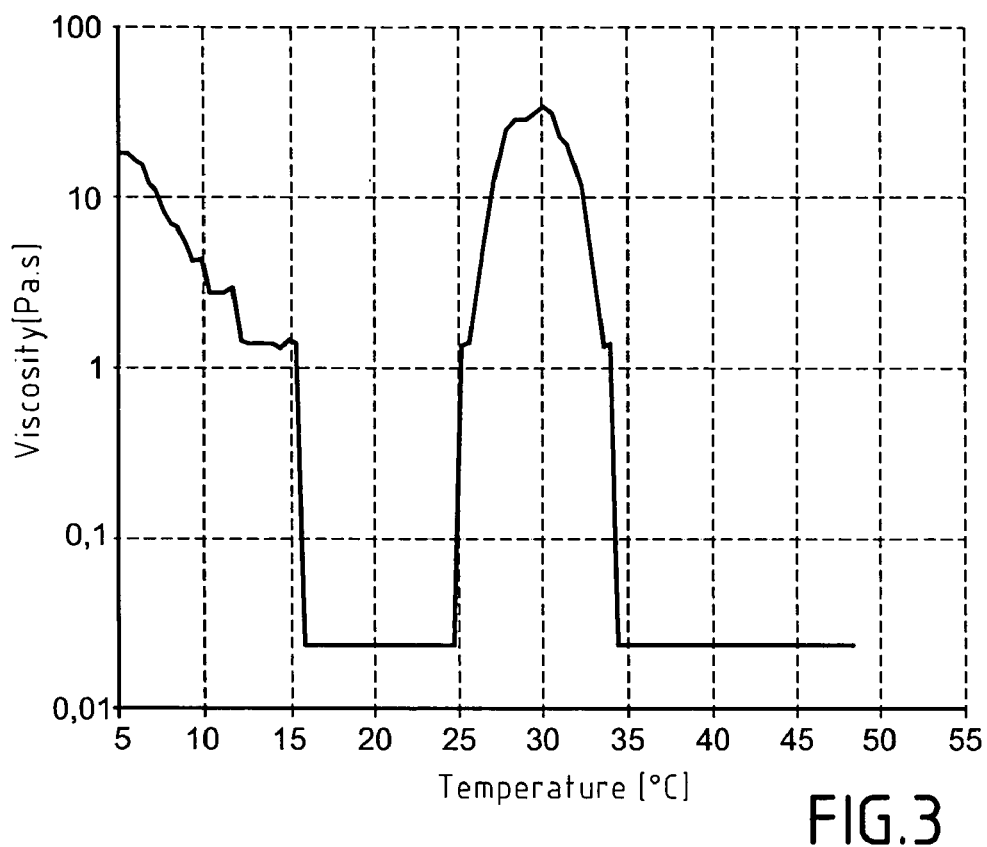
FIG. 3 shows a viscosity curve of a gel obtained according to Example 4.

FIG. 3 gives the variations in viscosity of the gel obtained with 5% by weight of the thermosensitive polymer synthesised in accordance with this Example, as a function of temperature under a shearing speed of 0.3/s.

Example 5

In this synthetic-example, an improved thermosensitive polymer is prepared having branches, which bear segments of poly(ethylene oxide) of molar mass of 750 g.

The synthesis is carried out in two steps; a first step consisting in preparing a first polymer in accordance with the first step of Example 4 and a second step during which the monohydroxylated poly(ethylene oxide) is introduced when only 26% of the initial isocyanate functions remain. The reaction is continued for 24 hours. The gel formulated with 5% of this polymer has a maximum viscosity at 37° C. and is very dense.

Figure 4:
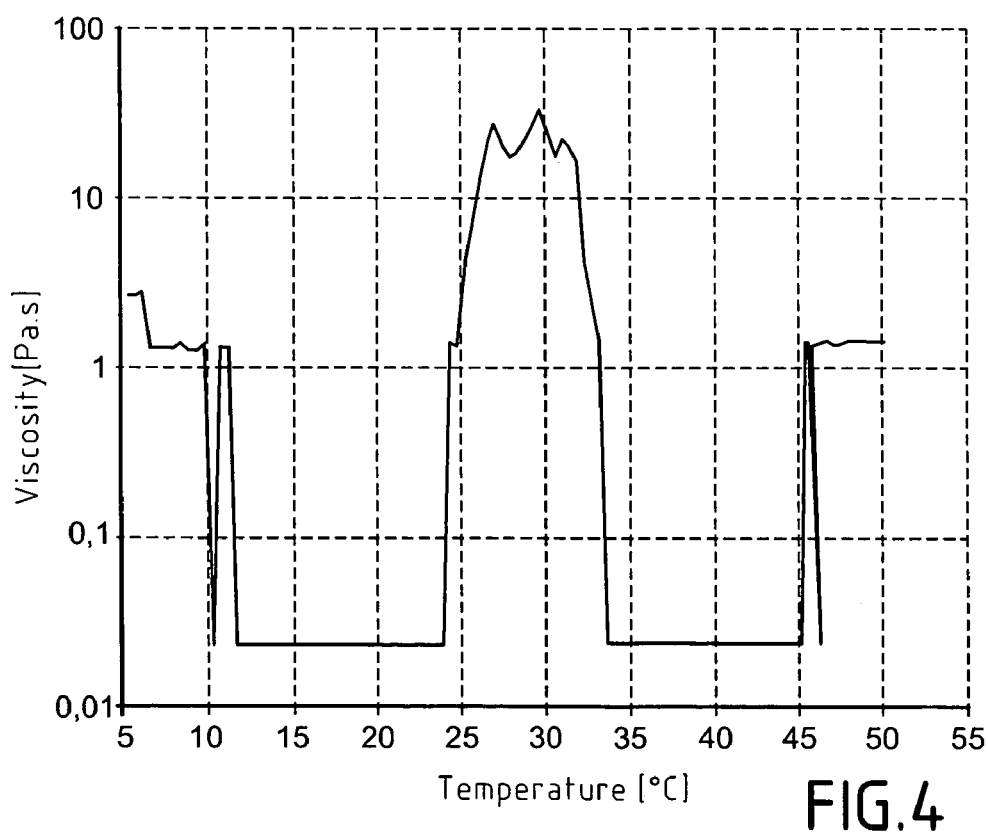
FIG. 4 shows a viscosity curve of a gel obtained according to Example 5.

FIG. 4 gives the viscosity curve of the thermoreversible gel obtained according to this Example, as a function of the temperature under a shearing speed of 0.3/s.

Example 6

In this example of synthesis, an improved thermosensitive polymer is prepared which has branches of allophanate and biuret type which bear segments of poly(ethylene oxide) of molar mass of 600 g/mol. The synthesis is carried out in two steps: a first step which consists in preparing a first polymer in the presence of a minimum amount of water, and a second step during which the terminating agent, i.e. the segment of monohydroxylated poly(ethylene oxide), is introduced.

In a first step, $7.69 \cdot 10^{-3}$ mole of Pluronic F127 polymer is dried under vacuum at 80° C. for 2 hours. 2-butanone (300 mL) containing 0.2 g of water is then added. After complete dissolution of the F127 polymer, $15.84 \cdot 10^{-3}$ mole of 4,4'-methylene biscyclohexyl diisocyanate are added dropwise over 10 minutes under a continuous flow of nitrogen. A tin-based catalyst is introduced 30 minutes after the end of the addition of the isocyanates, at the rate of 500 ppm, into the mixture which is maintained under the reflux of the solvent.

$13.98 \cdot 10^{-3}$ mole of the monohydroxylated poly(ethylene oxide) is introduced when only 42% of the initial isocyanate functions remain. The reaction is continued for 8 to 12 hours. The gel formulated with 7.5% of this polymer has a maximum viscosity at 35° C.

Figure 5:
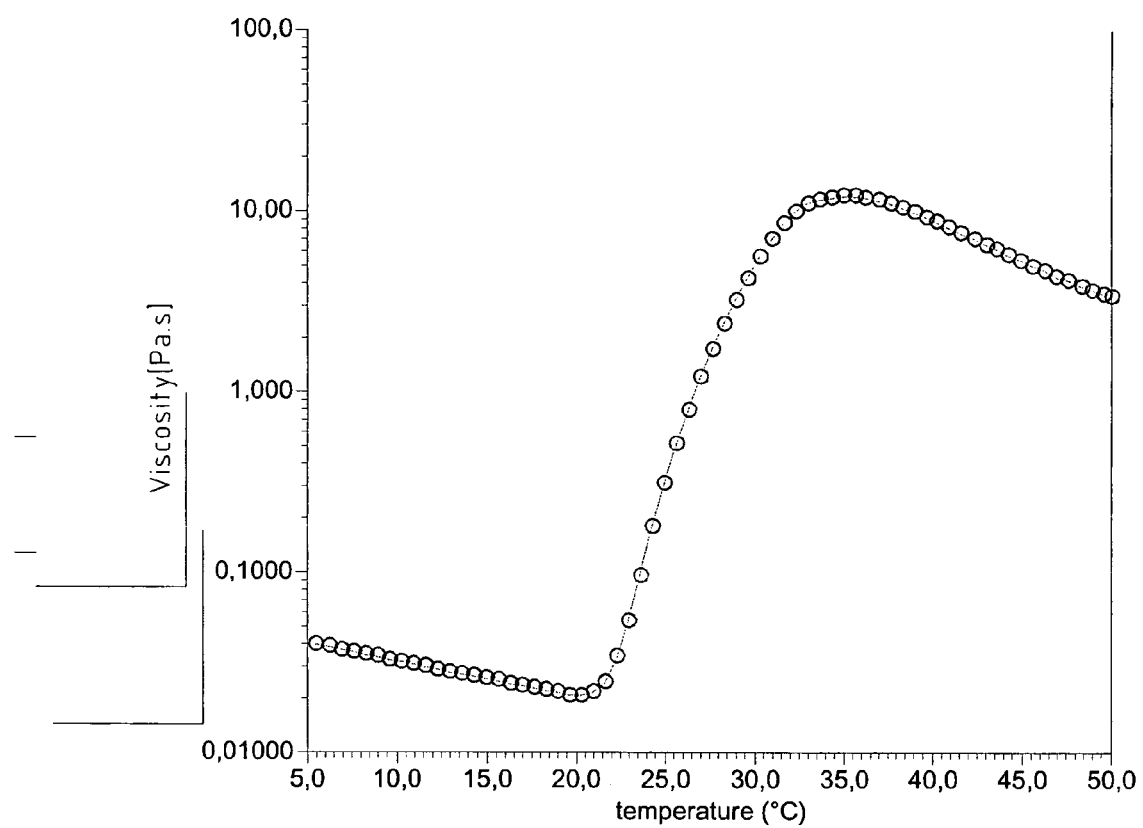
FIG. 5 shows a viscosity curve of a gel obtained according to Example 6.

FIG. 5 illustrates the rheological behaviour of the thermoreversible gel obtained according to this example as a function of temperature under a shearing speed of $10\ s^{-1}$.

Example 7

This synthetic example enables an improved thermosensitive polymer to be produced which has branches bearing long-chain aliphatic amines.

The synthesis comprises a first step which is identical to the first step of the preceding Example and a second step in which octadecyl amine is introduced as soon as only 18% of the initial isocyanate functions remain. The gel formulated with 8% of said polymer has a maximum viscosity at 37° C. and is very dense.

Example 8

$3.8 \cdot 10^{-3}$ mole of a polymer bearing the reference F127, marketed under the name of Pluronic is dissolved in 150 ml of 2-butanone, the whole being brought to 70° C. The F127 polymer is introduced without purification and contains 0.3% by mass of water ($7.6 \cdot 10^{-3}$ mole). $1.7 \cdot 10^{-2}$ mole of 4,4'-methylene biscyclohexyl di-isocyanate are then added dropwise to the mixture over 10 minutes under a continuous flow of nitrogen. A tin-based catalyst is introduced 30 minutes after the end of the addition of the isocyanates, at the rate of 2,000 ppm, into the mixture which is maintained under reflux of the solvent for around 48 hours.

When the whole of the NCO functions has been consumed, the polymer is collected by precipitation in diethyl ether.

Example 9

This synthetic example enables an improved thermosensitive polymer to be produced which has a higher proportion of urea groups as well as branches.

The synthesis is carried out in two steps; a first step consisting in preparing a first polymer by reaction of 3.8·10⁻³ mole of non-dried F127 Pluronic polymer containing 0.3% by mass of water (7.6·10⁻³ mole) and 0.14 g of added water (7.6·10⁻³ mole) with 4.4·10⁻² mole of 4,4'-methylene biscyclohexyl di-isocyanate added dropwise over 10 minutes under a continuous flow of nitrogen. A tin-based catalyst is introduced 30 minutes after the end of the addition of the isocyanates, at the rate of 500 ppm into the mixture which is maintained under the reflux of the solvent. When around 81% of the isocyanate functions have been consumed, 2.9·10⁻³ mole of 2,2-(bis hydroxymethyl) butyric acid are added. The polycondensation is continued for 24 hours at 70° C. until the complete disappearance of the initial isocyanate functions. The polymer is collected by precipitation in diethyl ether. The gel formulated with 5% of this polymer has, in solution, a dynamic viscosity of 3,000 Pa·s under a shearing speed of $0.003s^{-1}$.

What is claimed is:

1. A hydrosoluble thermosensitive polymer which comprises polyoxyalkylene triblock linear chains in more than 80% by weight of said thermosensitive polymer, said linear chains consisting of blocks of poly(ethylene oxide) (PEC) and of blocks of poly(propylene oxide) (PPO) in the form of PEO-PPO-PEO with a formula:

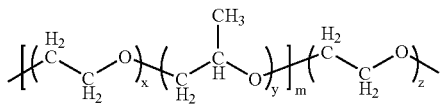

in which, 20<x <120, 20<y <120, 20<z <120, and m>0;
said linear chains are linked together by one or more organic linking groups which are bonded to said linear chains by either a carbamate bond or a urea bond; and both said carbamate bond and urea bond are present in said polymer.

2. The thermosensitive polymer of claim 1, wherein said polymer has two termini and said two termini are both an organic group bonded to said linear chains via a carbamate and/or urea bond.

3. The thermosensitive polymer of claim 1, wherein said organic linking group is selected from the group consisting of:

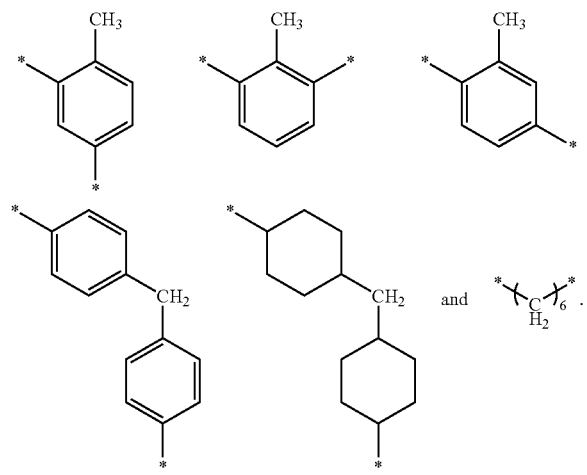

4. The thermosensitive polymer of claim 1, wherein said polymer has at least one of its termini comprising an organic group bonded to said linear chains via a carbamate bond and/or a urea bond.

5. The thermosensitive polymer of claim 4 wherein said organic group is selected from the group consisting of:

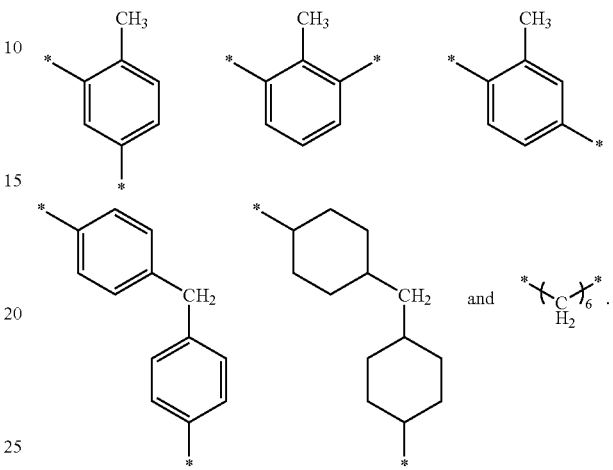

6. The thermosensitive polymer of claim 4 wherein said organic group comprises acid moieties.

7. The thermosensitive polymer of claim 4 wherein said organic group comprises tertiary amine moieties.

8. The thermosensitive polymer of claim 4 wherein said organic group comprises a chain of monohydroxylated poly (ethylene oxide) moieties.

9. The thermosensitive polymer of claim 1 which comprises branches bonded via allophanate and/or biuret bonds.

10. The thermosensitive polymer of claim 4 wherein said organic group has branches bonded via allophanate and/or biuret bonds.

11. A thermosensitive polymer having a general formula:

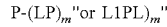

in which 1≦m"≦5
P represents linear chains in the form of PEO-PPO-PEO with a formula:

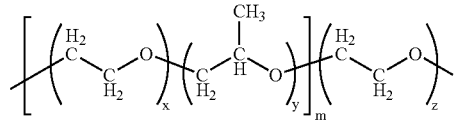

in which, 20<x<120, 20<y<120, 20<z<120, and m>0;
L represents one or more organic linking groups selected from the group consisting of:

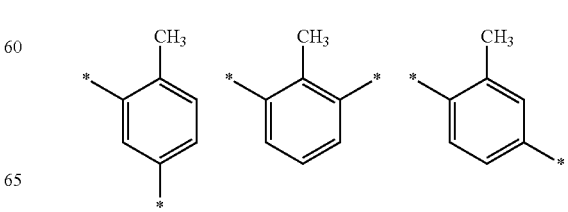

-continued

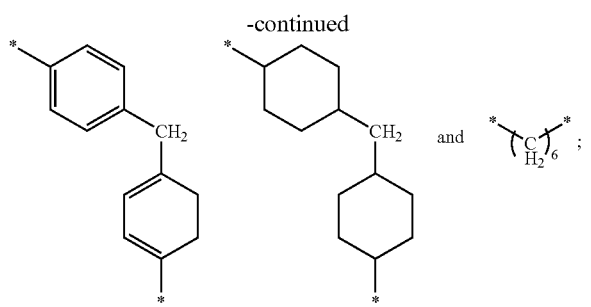

wherein said linear chains P comprising more than 80% by weight of said thermosensitive polymer, said linear chains P and said organic linking group L are bonded together via a carbamate bond or a urea bond; and both said carbamate bond and urea bond are present in said polymer.

12. The thermosensitive polymer of claim 11 in which said carbamate bond is a urethane funtional moiety.

13. A thermosensitive polymer having a general formula:

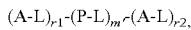

or

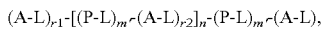

in which m', r1, and r2≧1;

P represents linear chains in the form of PEO-PPO-PEO with a formula:

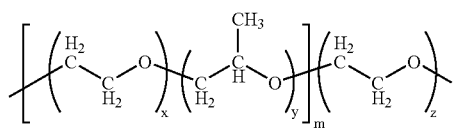

in which, 20<x<120, 20<y<120, 20<z<120, and m>0;

L represents one or more organic linking groups selected from the group consisting of:

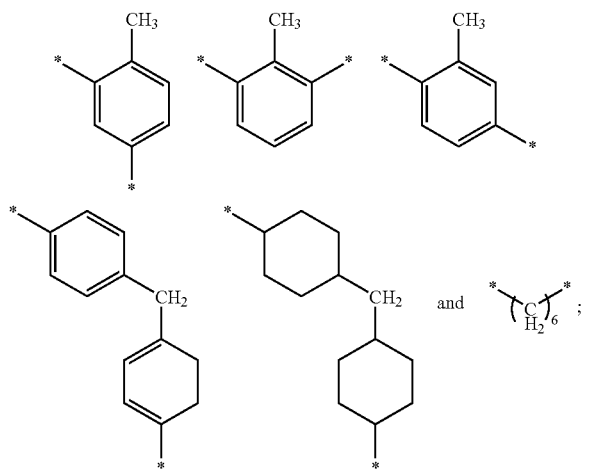

A represents organic moieties selected from the group consisting of acid blocks, tertiary amine blocks, and poly(ethylene oxide) blocks;

wherein said linear chains P comprising more than 80% by weight of said thermosensitive polymer, said linear chains B, said organic linking group L and said organic moiety A are linked together via a carbamate bond or a urea bond; and hoed said carbamate bond and urea bond are present in said polymer.

14. A thermosensitive polymer represented by

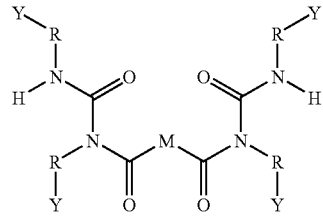

wherein, M is a thermosensitive polymer which comprises polyoxyalkylene triblock linear chains in more than 80% by weight of said thermosensitive polymer, said linear chains consisting of blocks of poly(ethylene oxide) (PEO) and of blocks of poly(propylene oxide) (PPO) in the form of PEO-PPO-PEO with a formula:

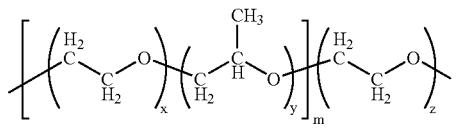

in which, 20<x<120, 20<y<120, 20<z<120, and m>0; said linear chains are linked together by one or more organic linking groups which are bonded to said linear chains by either a carbamate bond or a urea bond; and both said carbamate bond and urea bond are present in said polymer;

R is an organic linking group selected from the group consisting of:

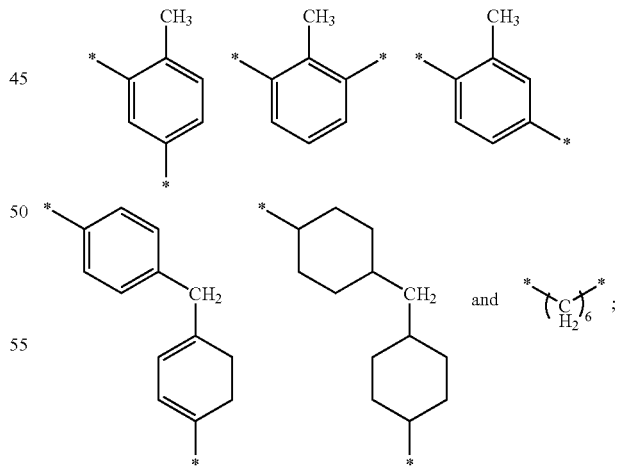

Y is a terminal ethyl or methyl function, an amino group, or another thermosensitive polymer;

where R is bonded with Y via a carbamate bond and/or a urea bond.

15. A method of synthesizing an improved hydrosoluble thermosensitive polymer as claimed in claim 1, which method comprises reacting at least one linear polymer P of thermosensitive PEO-PPO-PEO polyoxyalkylene triblock type having at least one terminal hydroxy function, in a solvent medium! with at least one organic molecule which bears at least one isocyanate function, in the presence of water in the reaction medium, wherein said at least one linear polymer P of thermosensitive PEO-PPO-PEO polyoxyalkylene triblock type having at least one terminal hydroxy function, said at least one organic molecule which bears at east one isocyanate function and said water being present in respective proportions effective to obtain a hydrosoluble thermosensitive polymer as claimed in claim 1 comprising more than 80% by weight of chains consisting of PEO-PPO-PEO linked together via carbamate bonds and urea bonds, and wherein said polymer P is of generic formula:

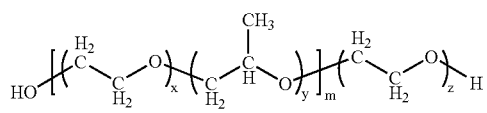

in which, 20<x <120, 20<y <120, 20<z <120, and m>0.

16. The method of claim 15 which is carried out in the presence of 0.1% to 0.6% of water by mass with respect to the terpolymer.

17. The method of claim 15 wherein said polymer P has at least two terminal hydroxy functions.

18. The method of claim 15 wherein the organic molecule comprises two isocyanate functions.

19. The method of claim 18 wherein the organic molecule is selected from the group consisting of

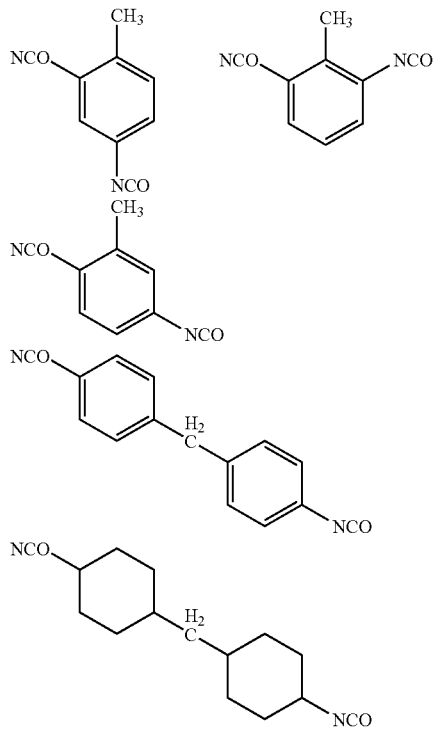

-continued

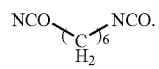

20. The method of claim 15 wherein at least one other organic molecule which hears at least one hydroxy function is added.

21. The method of claim 20 wherein said other organic molecule further comprises at least one carboxylic acid function.

22. The method of claim 21 wherein said other molecule is of formula:

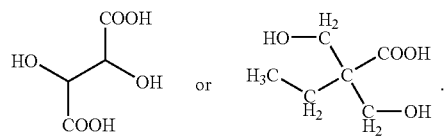

23. The method of claim 20 wherein said other organic molecule comprises at least one tertiary amine function.

24. The method of claim 23 wherein said other molecule is of formula:

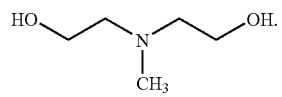

25. The method of claim 20 wherein said other molecule is a monohydroxylated poly(ethylene oxide).

26. A thermoreversible gel obtained from a solution of at least one thermosensitive polymer of claim 1.

27. A thermoreversible gel obtained from a solution of at least one thermosensitive polymer of claim 4.

28. The thermoreversible gel of claim 26 which comprises 1 to 10% by weight of said thermosensitive polymer.

29. The thermoreversible gel of claim 26 which contains 0.05 to 0.1% by weight of cross-linked poly(carboxylic acid).

30. The thermoreversible gel of claim 29 which contains 1 to 2.5% by weight of thermosensitive polymer.

31. The thermoreversible gel of claim 27 which comprises 1 to 10% by weight of said thermosensitive polymer.

32. The thermoreversible gel of claim 27 which contains 0.05 to 0.1% by weight of cross-linked poly(carboxylic acid).

33. The thermoreversible gel of claim 30 which contains 1 to 2.5% by weight of said thermosensitive polymer.

* * * * *